US010342749B2

(12) United States Patent
Baker et al.

(10) Patent No.: US 10,342,749 B2
(45) Date of Patent: Jul. 9, 2019

(54) ANTIPERSPIRANT COMPOSITIONS COMPRISING ALUMS

(71) Applicant: Conopco, Inc., Englewood Cliffs, NJ (US)

(72) Inventors: Michael Richard Baker, Chester (GB); Kevin Ronald Franklin, Wirral (GB); Robert Edward Marriott, Wirral (GB); Joanne Elizabeth Stockton, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/531,248

(22) PCT Filed: Nov. 11, 2015

(86) PCT No.: PCT/EP2015/076352
§ 371 (c)(1),
(2) Date: May 26, 2017

(87) PCT Pub. No.: WO2016/096264
PCT Pub. Date: Jun. 23, 2016

(65) Prior Publication Data
US 2017/0333308 A1 Nov. 23, 2017

(30) Foreign Application Priority Data
Dec. 15, 2014 (EP) .................................. 14197904

(51) Int. Cl.
A61K 8/26 (2006.01)
A61Q 15/00 (2006.01)
A61K 8/19 (2006.01)
A61K 8/20 (2006.01)
A61K 8/02 (2006.01)
A61K 8/04 (2006.01)
A61K 8/92 (2006.01)

(52) U.S. Cl.
CPC .............. A61K 8/26 (2013.01); A61K 8/0229 (2013.01); A61K 8/046 (2013.01); A61K 8/19 (2013.01); A61K 8/20 (2013.01); A61K 8/922 (2013.01); A61Q 15/00 (2013.01); A61K 2800/31 (2013.01)

(58) Field of Classification Search
None
See application file for complete search history.

(56) References Cited

U.S. PATENT DOCUMENTS

| 133,430 | A | 11/1872 | Gamgee |
| 3,963,833 | A | 6/1976 | DeSalva |
| 5,534,246 | A | 7/1996 | Herb |
| 5,788,956 | A | 8/1998 | De Lacharriere et al. |
| 5,955,065 | A | 9/1999 | Thong et al. |
| 6,139,824 | A | 10/2000 | Ribery |
| 2003/0049219 | A1* | 3/2003 | Lemoine ............... A61K 8/02 424/66 |
| 2006/0099161 | A1 | 5/2006 | Nakane et al. |
| 2010/0047296 | A1 | 2/2010 | Banowski et al. |
| 2012/0328549 | A1 | 12/2012 | Edelson et al. |
| 2014/0227215 | A1 | 8/2014 | Baker |
| 2014/0308215 | A1 | 10/2014 | Baker |

FOREIGN PATENT DOCUMENTS

| CN | 101492597 | | 7/2009 |
| EP | 1974716 | | 10/2008 |
| EP | 2574327 | | 4/2013 |
| FR | 2978036 | | 1/2013 |
| GB | 2076289 | | 12/1981 |
| JP | 5112440 | | 5/1993 |
| JP | 2007145771 | | 6/2007 |
| JP | 2008303123 | | 12/2008 |
| WO | WO02069914 | | 9/2002 |
| WO | WO2008120976 | | 10/2008 |
| WO | WO2010078917 | | 7/2010 |
| WO | WO2011076569 | | 6/2011 |
| WO | WO 2013/013903 | * | 1/2013 ............... A61K 8/25 |
| WO | WO2013013902 | | 1/2013 |
| WO | WO2013013903 | | 1/2013 |
| WO | WO2013045269 | | 4/2013 |
| WO | WO2013045270 | | 4/2013 |

(Continued)

OTHER PUBLICATIONS

Rules and, Federal Register 2003 68 34273-34292, Jun. 9, 2003, pp. 34283-34292, v. 68, No. 110.
Bennett, Two Thousand Formulas, Recipes & Trade Secrets: The Classic Do-It-Yourself Book of Practical Everyday Chemistry, Cosmetics and Drugs, 2004, p. 73; XP009171485, ., Bennett H. Feral House, US.
Milne, G.W.A. Gardner's Commercially Important Chemicals: Synonyms, Trade Names, & Properties, Wiley, Jan. 1, 2005, pp. 23-24, vol. 38, US.
Zhao Tian'en et al., Handbook of External Drugs in Dermatology, Handbook of External Drugs in Dermatology, Apr. 30, 1981, With partial translation., 1st Edition, Shandong Science and Technology Press.
Search Report in EP14197904, dated May 20, 2015.

(Continued)

Primary Examiner — Jake M Vu
(74) Attorney, Agent, or Firm — Greenberg Traurig, LLP

(57) ABSTRACT

An antiperspirant composition having less than 2% free water and comprising a first salt that is $M(i)Al(SO_4)_2$ or $Al_2(SO_4)_3$ and a second salt that is $CaX_2$, wherein X is $Cl^-$, $Br^-$, $I^-$, $NO_3^-$ or mixture thereof, wherein the first salt and the second salt are formulated or contained in a manner that prevents physical interaction between these two components prior to their application and wherein the product also comprises a third salt which is an inorganic base selected from metal hydroxide or carbonate or metal oxide having a water solubility of at least 0.01 $g/dm^3$ at 20° C.

12 Claims, No Drawings

(56) References Cited

FOREIGN PATENT DOCUMENTS

WO     WO2014161792     10/2014

OTHER PUBLICATIONS

Search Report in PCTEP2015076352, dated Dec. 23, 2015.
Written Opinion 2 in PCTEP2015076352, dated Nov. 10, 2016.
Written Opinion EP14197904, dated May 20, 2015.
IPRP2 in PCTEP2015076352, dated Mar. 10, 2017.
Written Opinion in PCTEP2015076352, dated Dec. 23, 2015.

\* cited by examiner

ANTIPERSPIRANT COMPOSITIONS COMPRISING ALUMS

The present invention is in the field of cosmetic compositions, in particular antiperspirant compositions and their use in reducing perspiration.

A variety of antiperspirant compositions have been marketed for many years. They serve to reduce perspiration, particularly following application to the surface of the body. Such compositions are typically considered cosmetic products, although certain countries do classify the active ingredients most commonly used in such compositions as pharmaceutical agents. The compositions are most commonly applied to the underarm regions of the human body.

The active ingredients conventionally used in antiperspirant compositions are astringent chlorohydroxide salts of aluminium and/or zirconium. These active ingredients are synthetic in origin, prepared in chemical plants and generally involving relatively advanced chemical processing steps. Such processing is not only expensive, but can also have significant environmental impact in terms of energy consumption.

Consumers are increasingly desirous of applying only "natural" ingredients and treatments to their body. Synthetic ingredients, in particular "active" ingredients, are often considered unsuitable for such application by consumers. There are a number of natural ingredients available that deliver some degree of deodorancy benefit when applied to the surface of the human body, but these ingredients are typically not capable of delivering a significant antiperspirancy benefit, i.e., they do not suppress perspiration to an extent that consumers would find acceptable. Hence, there is a problem in achieving good antiperspirancy using active ingredients that are natural ingredients.

Alum salts have been disclosed as suitable for use in a range of deodorant compositions and, indeed, such products have been marketed.

U.S. Pat. No. 6,139,824 (L'Oreal, 2000) discloses the use of potassium alum in water-in-oil emulsions for deodorising the body. This patent also references several other publications in which potassium alum is used in aqueous and aqueous/ethanol solutions and in suspension sticks.

EP 1,974,716 A (Sara Lee, 2007) and WO 08/120976 (Sara Lee, 2008) disclose cosmetic compositions, for instance deodorant compositions, comprising at least partially dehydrated aluminium sulphate and a carrier liquid other than water.

WO 2013/045270, WO 2013/045269, and WO 2014/161792 (Unilever, 2013-14) disclose antiperspirant compositions comprising alum and calcium chloride and selected further components.

Crystal Spring Ltd. offer or have offered a range of natural deodorants based upon the deodorising effect of potassium alum.

Green Bear UK Ltd. offer or have offered a crystal alum deodorant stick.

U.S. Pat. No. 5,534,246 (Helen Curtis, 1996) discloses water-in-oil emulsion antiperspirant compositions in which alum salts are optional components; however no formulations containing alum salts are exemplified.

U.S. Pat. No. 133,430 (John Gamgee, 1872) discloses the manufacture of a deodorising powder by mixing/grinding together aluminium sulphate (sulphate of alumina or "alum") and calcium chloride.

Other publications, such as U.S. Pat. No. 5,955,065 (Gillette, 1999), have described the use of water soluble calcium salts to enhance the performance of conventional antiperspirant actives. The chemistry described in such publications involves the enhancement of peaks 3 and 4 on the HPLC trace of such antiperspirant actives. The species responsible for these peaks are not generated in the methods described herein and the chemistry behind the present invention is entirely different (vide infra).

An objective of the present invention is to provide effective antiperspirant compositions the manufacture of which involves relatively low cost and relatively little environmental impact. In addition, the method and products of the invention may be seen as having good "natural" credentials, involving natural antiperspirant ingredients or at least naturally-derived antiperspirant ingredients. Further, the present invention discloses antiperspirant compositions that minimise or reduce irritation on application to the human skin.

A further objective of the present invention is to provide high efficacy, low irritancy antiperspirant compositions.

A further objective of the present invention is to provide a highly effective method of reducing perspiration from the human skin and it is a particular objective that said method does not involve the use of synthetic aluminium and/or zirconium chlorohydroxide antiperspirant actives such as aluminium chlorohydrate and/or does not cause significant irritation to the skin.

In a first aspect of the present invention, there is provided an antiperspirant composition having less than 2% free water and comprising a first salt that is $M(i)Al(SO_4)_2$ or $Al_2(SO_4)_3$ and a second salt that is $CaX_2$, wherein X is $Cl^-$, $Br^-$, $I^-$, $NO_3^-$ or mixture thereof, wherein the first salt and the second salt are formulated or contained in a manner that prevents physical interaction between these two components prior to their application and wherein the product also comprises a third salt which is an inorganic base selected from metal hydroxide or carbonate or metal oxide having a water solubility of at least 0.01 $g/dm^3$ at 20° C.

In a second aspect of the present invention, there is provided a method for reducing perspiration from the human skin comprising the topical application of all components of a product according to the first aspect of the invention.

In a third aspect of the present invention, there is provided a method for reducing perspiration comprising the topical application of a composition according to the third aspect of the invention to the surface of the human body.

In a fourth aspect of the present invention, there is provided a method of manufacture of an antiperspirant composition according to the first aspect of the invention.

The method for reducing perspiration described herein is for reducing perspiration from the surface of the human body, in particular from the underarm areas and the feet and especially from the underarm areas, otherwise known as the axillae.

The method for reducing perspiration may generally be considered a cosmetic method and products used in achieving the method, cosmetic products. That being said, the method can be extremely effective and may be also used to treat the medical condition of extreme sweating known as hyperhidrosis.

The method typically involves topical application of an alum salt, calcium chloride and inorganic base directly to the surface of the human body. In an alternative embodiment, the salts may be applied indirectly to the surface of the human body, for example by application of said salts onto a wipe which is in turn applied to the surface of the human body.

When the salts used in the present invention are applied to the surface of the human body, it is hypothesised that fluids derived from the sweat glands at least partially dissolve and hence mobilise the salts, allowing them to interact and thereby deliver a good antiperspirancy benefit.

Herein, the term "dried powder" should be understood to include both crystalline and amorphous states of matter. Such powders have a water content that is reduced from that of the most hydrated natural salt of the particular salt being used. More is said concerning preferred "dried powders" in the paragraphs describing preferred alum salts and preferred calcium chloride salts.

Herein, the term "anhydrous" should be understood to mean having less than 2% by weight of free water; "free water" being water other than the water of hydration associated with any particular component. Preferably, anhydrous compositions have less than 1% by weight free water and more preferably less than 0.5%.

It is preferred that anhydrous compositions have a total water content (including water of hydration associated with components therein) of less than 10% by weight, and more preferably less than 5%.

Herein, the term alum salt as used in the present description means aluminium sulphate (sometimes called "alum") or any double sulphate of aluminium and a univalent metal ion selected from potassium, sodium, or ammonium. It does not include alum salts that are double sulphates of a univalent metal and a trivalent metal other than aluminium, such as chromium (III) or iron (III).

Alum salts for use in the present invention are potassium alum, ammonium alum, sodium alum and aluminium sulphate. That is to say:

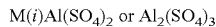

wherein M(i) is $K^+$, $Na^+$, $NH_4^+$ or mixture thereof.

Preferred alum salts are ammonium and potassium alum, in particular potassium alum.

Preferred alum salts have a reduced content of water, that is to say, they are at least partially dehydrated. They may alternatively be described as dried powders (vide supra). It has been found that use of such salts in compositions also comprising calcium chloride improves ease of formulation and/or leads to improved storage stability for said compositions. Reducing the water content of the alum serves as a means for restricting chemical interaction between it and the calcium chloride prior to their application to the skin.

Potassium alum dodecahydrate has been found to be particularly difficult to formulate with calcium chloride; however, reducing its water content by 25% or greater can lead to acceptable compositions. In general, preferred alum salts for use in present invention have a water content of less than 35% by weight. Particularly preferred alum salts have a water content of less than 28% by weight and especially preferred alum salts have a water content of less than 20% by weight. When water is present, it is typically present as water of hydration.

The alum salt used in the present invention is typically milled to give it a reduced particle size. In preferred embodiments, the particle size distribution of the alum salt is such that its D50 is less than 75 microns and more preferably less than 50 microns. The particle size distribution of the alum salt is preferably such that less than 5% and more preferably less than 1% by weight of the particles have a particle size of greater than 120 microns.

The particle size distribution of the alum salt may advantageously be measured using a light scattering method on a Malvern Mastersizer 2000. The powder is dispersed in silicone fluid (DC245) and the results are analysed assuming a particle refractive index of 1.55 and imaginary refractive index of 0.001.

The calcium chloride used in the present invention may be substituted in whole or in part by other salts according to the general equation:

wherein X is $Cl^-$, $Br^-$, $I^-$, $NO_3^-$ or mixture thereof.

Herein, references to calcium chloride are in their broadest sense references to $CaX_2$ as defined above.

Independently and collectively, X is most preferably $Cl^-$.

It should also be noted that a water soluble strontium salt such as strontium chloride could be used as an alternative to calcium chloride.

The calcium chloride used in the present invention may be anhydrous or hydrated, such as calcium chloride dihydrate, although anhydrous calcium chloride is preferred in many embodiments. Preferably, the calcium chloride is a dried powder (vide supra). The calcium chloride preferably has a water content of 25% or less, more preferably less than 15%, and most preferably less than 8% by weight. When water is present, it is typically present as water of hydration.

The water content of the calcium chloride is particularly important when it is formulated with alum salt. In compositions comprising both calcium chloride and alum salt, it is essential that the calcium chloride has a water content of 25% or less, unless there is some other means for restricting chemical interaction between it and the alum salt prior to their application to the skin. Suitable calcium chloride salts for such compositions include calcium chloride dihydrate and anhydrous calcium chloride, with anhydrous calcium chloride being preferred. It should be noted, however, than anhydrous calcium chloride as obtained from some suppliers can include up to about 14% by weight of water of hydration.

The calcium chloride used in the present invention is typically milled to give it a reduced particle size. In preferred embodiments, the particle size distribution of the calcium chloride is such that its D50 is less than 100 microns, more preferably less than 75 microns and most preferably less than 50 microns. The particle size distribution of the calcium chloride is preferably such that less than 5% and more preferably less than 1% by weight of the particles have a particle size of greater than 120 microns.

The particle size distribution of the calcium chloride salt may advantageously be measured using a light scattering method on a Malvern Mastersizer 2000. The powder is dispersed in silicone fluid (DC245) and the results are analysed assuming a particle refractive index of 1.55 and imaginary refractive index of 0.001.

Important to the present invention is the timely triggering of the following chemical reaction:

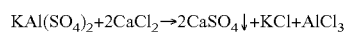

Or

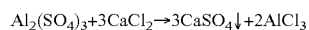

In the top equation, the potassium ion ($K^+$) may be substituted by sodium ($Na^+$) or ammonium ($NH_4^+$) and in both equations the calcium ion ($Ca^{2+}$) may be substituted by strontium ($Sr^{2+}$).

In both equations, the chloride ion used may be substituted by bromide, iodide, or nitrate. Thus, the calcium or strontium chloride could equally well be calcium or strontium bromide, iodide, nitrate or any mixture thereof.

The stoichiometry of the above equations requires one mole of alum to two moles of calcium chloride in the first and one mole of alum to three moles of calcium chloride in the second. These equations set the basis for the preferred ratios of these components in compositions comprising both of these components. In such compositions, it is preferred that the molar quantity of calcium chloride exceeds the molar quantity of alum salt. It is also preferred that the quantity of calcium chloride at least matches that stoichiometrically required by the above equations, relative to the amount and type of alum present. This means that it is preferred that the molar ratio of calcium chloride to alum salt is at least 2:1.

In compositions comprising calcium chloride and sodium, potassium or ammonium alum as the major alum salt present, the molar ratio of calcium chloride to alum salt is preferably from 1:1 to 5:1, more preferably from 3:2 to 3:1, and most preferably about 2:1.

In compositions comprising calcium chloride and aluminium sulphate as the major alum salt present, the molar ratio of calcium chloride to alum salt is preferably from 2:1 to 6:1, more preferably from 5:2 to 4:1, and most preferably about 3:1.

It is important to the present invention that the reaction indicated above only occurs to a minimal extent before the components are delivered to the surface of the human skin. Premature reaction results in a physical state of matter which tends not to deliver the desired benefits; indeed, it is commonly extremely difficult to even apply said matter to the desired location.

The chemical reactions involved in the present invention may only occur when the ions making up the reactants have sufficient mobility. In certain preferred embodiments of the present invention, this mobility typically arises when the reacts dissolve in aqueous body fluids found on the surface of the human body.

Magnesium chloride is ineffective when used instead of calcium chloride because of the much greater water solubility of magnesium sulphate compared with calcium sulphate.

A third salt is essential to the functioning of the present invention, this salt being an inorganic base selected from metal hydroxide or carbonate or metal oxide having a water solubility of at least 0.01 g/dm$^3$ at 20° C.

The third salt is particularly important in delivering the low/reduced irritancy benefit of the invention.

Having a minimum water solubility for the metal oxide of at least 0.01 g/dm$^3$ at 20° C. has been found to be critical. In the course of their research, the present inventors found that zinc oxide (having a water solubility of 0.0016 g/dm$^3$ at 30° C.) was ineffective at mitigating irritation.

Preferred 'third salts' are inorganic bases having limited water solubility. In this regard, inorganic bases used in accordance with the invention preferably have a water solubility of less than 5 g/dm$^3$ at 20° C. and more preferably a water solubility of less than 2.5 g/dm$^3$ at 20° C. It has been found that inorganic bases with limited water solubility are superior in terms of reduced irritation without undue compromise to antiperspirancy performance.

Chemical classes from which preferred inorganic bases may be selected are metal oxides and hydroxides.

Preferred inorganic bases in accordance with the invention are salts of calcium or magnesium, in particular calcium oxide or hydroxide or magnesium oxide or hydroxide. Calcium carbonate or magnesium carbonate may also be effective, but can lead to problems due to carbon dioxide production.

Especially preferred inorganic bases are calcium hydroxide and magnesium hydroxide.

The ratio of the "first salt" (alum) to the "third salt" (inorganic base) is particularly important. If it is too high, insufficient reduction of irritation may be found. If it is too low, there can be a loss in antiperspirancy performance.

It is preferred that the molar ratio of the first salt to the third salt is at least 1:1, more preferably at least 1.1:1, and most preferably at least 1.2:1.

It is preferred that the molar ratio of the first salt to the third salt is up to 10:1 and more preferably up to 4:1.

It is particularly preferred that the molar ratio of the first salt to the third salt is from 1:1 to 10:1 and it is especially preferred that the molar ratio is from 1.2:1 to 4:1.

The preferred ratios of first salt to third salt as indicated in the above three paragraphs are particularly important within the preferred molar ratio of second salt (calcium chloride) to first salt (alum), that is to say, when the molar ratio of second salt (calcium chloride) to first salt (alum) is from 1:1 to 5:1 and especially when the molar ratio of second salt (calcium chloride) to first salt (alum) is from 3:2 to 3:1.

Other components may also be included in compositions used in accordance with the invention.

A component frequently included is a cosmetically acceptable carrier material. Compositions preferably comprise the carrier material at a level of from 20% to 90%, or more preferably from 30% to 85% of the weight of the composition, excluding any volatile propellant present.

Such carrier materials are typically liquid, by which is meant liquid at ambient temperature and pressure (20° C. and 1 atmosphere). Preferably, such carrier substances are anhydrous, as described hereinabove, particularly when co-formulated with the first salt and second salt and especially when formulated with the first salt, second salt and third salt in accordance with the present invention. Preferably, carrier materials contain less than 2%, more preferably less than 1 and most preferably less than 0.5% by weight free water.

Preferred liquid carrier materials comprise an emollient oil. In the course of their research, the present inventors found that such oils can augment irritation mitigation when combined with the third salt (inorganic base); i.e. the presence of an emollient oil further reduces any irritation caused by the compositions of the invention, when used in combination with the third salt.

Preferred carrier materials are hydrophobic. Hydrophobic liquid carrier materials particularly suitable for use are liquid silicones, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, non-silicone hydrophobic liquids may be used. Such materials include mineral oils, hydrogenated polyisobutene, polydecene, paraffins, isoparaffins of at least 10 carbon atoms, ether oils such as PPG-14 butyl ether, and aliphatic or aromatic ester oils (e.g. triethyl hexanoin, isopropyl myristate, lauryl myristate, isopropyl palmitate, diisopropyl sebacate, diisopropyl adipate, or $C_8$ to $C_{18}$ alkyl benzoates). Particularly preferred carrier materials are ester oils, in particular C12-15 alkyl benzoate, available as Finsolv TN from Finetex.

Preferably the liquid carrier material comprises an emollient oil selected from sunflower seed oil and other triglyceride oils, in particular other unsaturated triglyceride oils. The fatty acid residues in the oils can comprise from one to three olefinic unsaturated bonds and often one or two. The olefinic bonds are typically in cis configuration. If two or three olefinic unsaturated bonds are present, they can be conjugated. The fatty acid residue can also be substituted by a hydroxyl group.

Suitable emollient oils include triglycerides of oleic acid, linoleic acid, linolenic acid or ricinoleic acid. It is especially desirable to employ triglycerides of oleic acid, linoleic acid or petroselenic acid or mixed esters of two or more of them.

Emollient oils containing one or more of such triglycerides include coriander seed oil, impatiens balsimina seed oil, parinarium laurinarium kernel fat, sabastiana brasilinensis seed oil, dehydrated castor seed oil, borage seed oil, evening primrose oil, aquilegia vulgaris oil, sunflower seed oil, and safflower oil. Other suitable emollient oils are obtainable from hemp and maize corn oil.

Sunflower seed oil is an especially preferred emollient oil for use in the present invention.

When an emollient oil selected from sunflower seed oil and other triglyceride oils is employed, it is typically included at a level of from 1% to 30%, and preferably at from 2% to 20% and more preferably from 3% to 15% by weight of the composition, excluding any volatile propellant present.

In some embodiments, polar organic solvents that may be employed include $C_1$-$C_4$ monohydric alcohols, for example ethanol and isopropanol, and polyols, for example propylene glycol, dipropylene glycol, glycerol, polyethylene glycol, and $C_2$-$C_8$ 1,2-alkanediols like 1,2-hexanediol.

Additional antiperspirant actives may also be included.

The total amount of antiperspirant actives, including alum salt and calcium chloride, incorporated in a composition is preferably from 0.5-50%, particularly from 1 to 30% and especially from 2% to 26% of the weight of the composition.

Antiperspirant actives used in addition to the alum salt and calcium chloride combination are often selected from astringent active salts, including in particular aluminium, zirconium and mixed aluminium/zirconium salts. Preferred additional antiperspirant actives are aluminium, zirconium and aluminium/zirconium halides and halohydrate salts, such as chlorohydrates.

Suitable aluminium halohydrates are defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts are known as activated aluminium chlorohydrates and are made by methods known in the art.

Suitable zirconium actives are represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof.

Antiperspirant complexes based on the above-mentioned astringent aluminium and/or zirconium salts can be employed. The complex often employs a compound with an amino acid, such as glycine.

The proportion of solid antiperspirant salt in a suspension composition normally includes the weight of any water of hydration and any complexing agent that may also be present in the solid active.

Additional deodorant actives may also be included. When employed, the level of incorporation is preferably from 0.01% to 3% and more preferably from 0.03% to 0.5% by weight. Preferred deodorant actives are those that are more efficacious than simple alcohols such as ethanol. Examples include quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred are polyhexamethylene biguanide salts (also known as polyaminopropyl biguanide salts), an example being Cosmocil CQ available from Arch Chemicals; 2',4,4'-trichloro-2-hydroxy-diphenyl ether (triclosan); and 3,7,11-trimethyldodeca-2,6,10-trienol (farnesol).

Other components particular to the type of composition in which the invention is used may also be included. Types of composition in which the invention may be used include, non-exclusively, sticks, soft solids, aerosols, and roll-ons.

Stick or soft solid compositions typically comprise one or more structurants or gellants, which serves to thicken the composition. Such thickeners, referred to as structurant systems, may be selected from those known in the art for such purpose. The present inventors have found the choice of structurants to be of particular importance when the alum salt and calcium chloride are included in the same composition. In such compositions, it has been found that particularly suitable structurant systems comprise:

1. stearyl alcohol as the major component, preferably in the presence of lesser amounts of polyethylene wax and hydrogenated castor oil; or
2. polyethylene wax as the major component, preferably in the presence of lesser amount of hydrogenated castor oil.

In general, structurant and gellants suitable for use in compositions according to the present invention may be classed as waxes or non-polymeric fibre-forming gellants.

"Waxes" may be defined as water-insoluble materials that are solid at 30° C. and preferably also at 40° C. They may be selected from hydrocarbons, linear fatty alcohols, silicone polymers, esters waxes or mixtures thereof.

Examples of hydrocarbon waxes include paraffin wax, ozakerite, microcrystalline wax and polyethylene wax, the last named desirably having an average molecular weight of from 300 to 600 and advantageously from 350 to 525.

Linear fatty alcohols commonly contain from 14 to 40 carbon atoms and often from 16 to 24. In practice, most contain an even number of carbon atoms and many comprise a mixture of compounds, even those that are nominally a single one such as stearyl alcohol.

Silicone polymer waxes typically satisfy the empirical formula:—

$$R\text{---}(SiMe_2\text{-}O\text{---})_x\text{---}SiMe_2R \qquad 1.$$

in which x is at least 10, preferably 10 to 50 and R represents an alkyl group containing at least 20 carbons, preferably 25 to 40 carbons, and particularly having an average linear chain length of at least 30 carbons; or

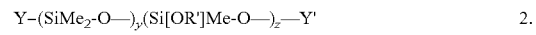

$$Y\text{-}(SiMe_2\text{-}O\text{---})_y(Si[OR']Me\text{-}O\text{---})_z\text{---}Y' \qquad 2.$$

in which Y represents $SiMe_2$-O, Y' $SiMe_2$, R' an alkyl of at least 15 carbons preferably 18 to 22 such as stearyl, y and z are both integers, totalling preferably from 10 to 50.

Examples of ester waxes include esters of $C_{16}$-$C_{22}$ fatty acids with glycerol or ethylene glycol, which can be isolated from natural products or more conveniently synthesised from the respective aliphatic alcohol and carboxylic acid.

"Non-polymeric fibre-forming gellants" are capable of being dissolved in a water-immiscible blend of oils at elevated temperature and on cooling precipitating out to form a network of very thin strands that are typically no more than a few molecules wide. One particularly effective category of such thickeners comprises N-acyl amino acid amides and in particular linear and branched N-acyl glutamic acid dialkylamides, such as in particular N-lauroyl glutamic acid di n-butylamide and N-ethylhexanoyl glutamic acid di n-butylamide and especially mixtures thereof. Such amido gellants can be employed in anhydrous compositions according to the present invention, if desired, with 12-hydroxystearic acid.

Other such non-polymeric fibre-forming gellants include 12-hydroxystearic acid amides, and amide derivatives of di- and tri-basic carboxylic acids as set forth in WO 98/27954, including notably alkyl N,N'dialkyl succinamides.

Further suitable structuring systems comprising non-polymeric fibre-forming gellants of this type are described in U.S. Pat. No. 6,410,003, U.S. Pat. No. 7,332,153, U.S. Pat. No. 6,410,001, U.S. Pat. No. 6,321,841, and U.S. Pat. No. 6,248,312.

The structurant or gellant is often employed in the stick or soft solid composition at a concentration of from 1.5 to 30%. When a non-polymeric fibre-forming gellants is employed as the major component of the structuring system, its concentration is typically in the range of from 1.5 to 7.5% by weight for amido gellants or mixtures of them and for 5 to 15% for ester or sterol gellants. When a wax is employed as the major component of the structuring system, its concentration is usually selected in the range of from 10 to 30% by weight, and particularly from 12 to 24% by weight.

Other types of structurant or gellant disclosed in the prior art may alternatively be employed.

Aerosol compositions suitable for use in accordance with the invention are characterised by comprising a propellant, typically a liquefied hydrocarbon or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquified hydrocarbon gases, and especially $C_3$ to $C_6$ hydrocarbons, including propane, butane, isobutane, pentane and isopentane and mixtures of two or more thereof. Preferred propellants are isobutane, isobutane/propane, butane/propane and mixtures of propane, isobutane and butane.

Other propellants that can be contemplated include alkyl ethers, such as dimethyl ether or compressed non-reactive gasses such air, nitrogen or carbon dioxide.

The propellant is typically the major component of aerosol compositions, often comprising from 30 to 99% weight and preferably comprising from 50 to 95% by weight.

In certain preferred embodiments, aerosol compositions may also comprise a liquid carrier material other than the propellant. These may be selected as appropriate from those previously mentioned, hydrophobic liquid carrier materials being especially preferred.

In certain preferred embodiments, aerosol compositions may also comprise a suspending agent, for example, a hydrophobically modified clay, such as disteardimonium hectorite (Bentone 38V), ex Elementis, typically at from 0.1 to 1.5% by weight.

Propylene carbonate may also be advantageously employed in aerosol compositions used in accordance with the present invention, typically at from 0.001 to 0.1% by weight.

Roll-on compositions suitable for use in accordance with the invention are typically suspension products, in particular suspensions of alum salt and calcium chloride in an anhydrous liquid carrier material (vide supra), hydrophobic liquid carrier materials being preferred.

Roll-on compositions preferably comprise a suspending agent, for example, a hydrophobically modified clay, such as disteardimonium hectorite (Bentone 38V), ex Elementis, typically at from 0.5 to 3% by weight.

Roll-on compositions preferably comprise a particulate sensory modifier, for example finely divided clay such as Aerosil 200, ex Evonik Degussa, typically at from 0.01 to 0.5% by weight.

Certain sensory modifiers are further desirable components in the compositions of the invention. Such materials are preferably used at a level of up to 20% by weight of the composition. Emollients, humectants, volatile oils, non-volatile oils, and particulate solids that impart lubrication are all suitable classes of sensory modifiers. Examples of such materials include cyclomethicone, dimethicone, dimethiconol, isopropyl myristate, isopropyl palmitate, talc, finely-divided silica (e.g. Aerosil 200), particulate polyethylene (e.g. Acumist B18), polysaccharides, corn starch, C12-C15 alcohol benzoate, PPG-3 myristyl ether, octyl dodecanol, C7-C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

In certain compositions, emulsifiers that are perfume solubilisers and/or wash-off agents are preferred additional components. Examples of the former include PEG-hydrogenated castor oil, available from BASF in the Cremophor RH and CO ranges, preferably present at up to 1.5% by weight, more preferably 0.3 to 0.7% by weight. Examples of the latter include poly(oxyethylene) ethers.

In many embodiments of the invention, fragrance is a desirable additional component. Suitable materials include conventional perfumes, such as perfume oils and also include so-called deo-perfumes, as described in EP 545,556, for example. Levels of incorporation are preferably up to 5% by weight, particularly from 0.1% to 3.5% by weight, and especially from 0.5% to 2.5% by weight. The fragrance may also be added in an encapsulated form, release being triggered post-application by hydrolysis or shear on the surface of the human body.

Further additional components that may also be included are colourants and preservatives at a conventional level, for example $C_1$-$C_3$ alkyl parabens.

The method of manufacture of products of the invention may involve independent manufacture of a first composition comprising alum salt, a second composition comprising calcium chloride, and packaging of the compositions in such a manner as to enable both compositions to be applied to the same portion of the human skin, whether sequentially or (preferably) simultaneously.

The method of manufacture of compositions according to the invention typically comprises the alum salt being reduced in water content prior to mixing with the calcium chloride in a carrier material. In such methods, the alum salt is preferably reduced in water content to less than 35%, more preferably less than 28% and most preferably less than 20% by weight.

EXAMPLES

The following examples illustrate certain specific embodiments of the invention and do not limit the scope of the invention. Examples according to the invention are indicated by numbers and comparative examples are indicated by letter. All amounts indicated are percentages by weight, unless otherwise indicated.

Specific Ingredient Details (1) Potassium alum (burnt alum) ex Brenntag. Water content 8-12%. Particle Size (D50) 17 micron.

(2) Anhydrous calcium chloride. Less than 7% water, ex Sigma-Aldrich, jet milled to give a particle size (D50) of 15-25 micron.

(3) Magnesium hydroxide, ex Sigma Aldrich, sieved to give a particle size (D50) of ~40 micron.

(4) Calcium hydroxide, ex Sigma Aldrich, particle size (D50)~7 micron.

Stick Examples

The stick compositions of Table 1 were prepared as follows. The oils (cyclomethicone and Finsolv TN) were blended together at 95° C. and the waxes (Castorwax MP80 and Polyethylene wax) were melted in with stirring. When the waxes were fully melted, each mixture was cooled to 85° C. The calcium chloride was then added, followed by the alum, and then, if employed, the inorganic base, these powders being fully dispersed into the mixture. Each mixture was then cooled to about 78° C. and, if employed, the sunflower seed oil and Aloe Vera was added and fully dispersed. Finally, the fragrance was added and dispersed. Each mixture was cooled to about 75° C. and poured into stick barrels.

The antiperspirancy efficacy of the stick compositions of Table 1 were compared with that of a non-antiperspirant body spray control. Test operators applied 0.3 g of each stick composition to one axilla and about 1.5 g of the body spray control to the other axilla of each panellist. This was done once each day for three days. After the third application, panellists were requested not to wash under their arms for the following 24 hours.

24 hours after the third and final product application, the panellists were induced to sweat in a hot-room at 40° C. (±2° C.) and 40% (±5%) relative humidity, for 40 minutes. After this period, the panellists left the hot-room and their axillae were carefully wiped dry. Pre-weighed cotton pads were then applied to each axilla of each panellist and the panellists re-entered the hot-room for a further 20 minutes. Following this period, the pads were removed and re-weighed, enabling the weight of sweat generated to be calculated. The sweat weight reduction (SWR) for each panellist was calculated as a percentage (% SWR) and the mean % SWR was calculated according to the method described by Murphy and Levine in "Analysis of Antiperspirant Efficacy Results", *J. Soc. Cosmetic Chemists,* 1991 (May), 42, 167-197.

TABLE 1

| | | Example | | | |
|---|---|---|---|---|---|
| Trade Name | Chemical Name | A | 1 | 2 | 3 |
| Finsolv TN | C12-15 alkyl benzoate | 30 | 30 | 30 | 30 |
| Castorwax MP80 | Hydrogenated castor oil | 2 | 2 | 2 | 2 |
| Performalene 400 | Polyethylene wax | 15 | 15 | 15 | 15 |
| Calcium Chloride | Calcium chloride | 7.16 | 7.16 | 7.16 | 7.16 |
| Potassium Alum | Potassium alum | 9.37 | 9.37 | 9.37 | 9.37 |
| Magnesium hydroxide | Magnesium hydroxide | — | 1 | 1 | 2 |
| Florasun 90 | Sunflower seed oil | — | — | 8 | — |
| Aloe Vera | Aloe Barbadensis leaf juice | — | — | 0.5 | — |
| | Fragrance | 1.5 | 1.5 | 1.5 | 1.5 |
| Xiameter PMX-0245 | Cyclomethicone | To 100 | To 100 | To 100 | To 100 |

The irritation potential of the stick formulations were measured using an exaggerated use protocol. Panelists (30 underarms per cell) applied approximately 0.25 g of one test product to one underarm. The 3 applications of the test products were spaced evenly through the day.

Erythema and dryness were assessed by a trained assessor at regular intervals throughout the test prior to product application on that day. Both attributes were ranked on a scale of 0 to 3.5 (8 point scale in units of 0.5). The reported Irritation scores are the sum of the scores for both attributes.

Panelists were also asked to report any self-perceived irritation (burning, itching, stinging). Adverse Events were recorded when the erythema or dryness scores reached or exceeded 3, or when the panelists reported significant levels of irritation and asked to stop using the product further.

Further testing of any product was stopped if more than 30% of panellists had an Adverse Event.

Results of hot-room and Irritation testing are given in Table 2.

TABLE 2

| | Mole ratio | SWR | Adverse events | | Irritation score | |
|---|---|---|---|---|---|---|
| Example | base:alum | (%) | 11 days | 29 days | 11 days | 29 days |
| A | Not applicable | 45 | 9 | * | 3.15 | * |
| 1 | 1:2 | 39 | 0 | 5 | 1.35 | 2.8 |
| 2 | 1:2 | 41 | 0 | 2 | 1.25 | 1.9 |
| 3 | 1:1 | 29 | — | — | — | — |

* Test stopped after 11 days due to Adverse Events.

From Table 2 it can be seen that Example 1 produces significantly lower irritation than Comparative Example A. Example 2 gave still lower irritation, illustrating the benefit of adding an emollient oil as well as the inorganic base. Both Example 1 and 2 gave good hot-room efficacies, i.e. good SWR.

Example 3 gave a significantly poorer hot-room efficacy than Example 1 or Example 2. It will be noted that the base to alum ratio is this example was outside the preferred range and this is the reason for the impaired hot-room efficacy. The irritancy of Example 3 was not tested, but would have been low.

Aerosols

The aerosol compositions of Table 3 were prepared as described below.

TABLE 3

| Ingredients* | Example |  |  |  |  |  |  |
|---|---|---|---|---|---|---|---|
|  | B | C | 4 | 5 | 6 | 7 | 8 |
| Cyclopentasiloxane | 6.646 | 7.066 | 6.946 | 6.866 | 6.816 | 6.768 | 6.638 |
| C12-15 Alkyl Benzoate | 2.5 | 0.72 | 0.72 | 0.72 | 0.72 | 0.72 | 0.72 |
| Sunflower seed oil | — | 1.28 | 1.28 | 1.28 | 1.28 | 1.28 | 1.28 |
| Disteardimonium Hectorite | 0.625 | 0.625 | 0.625 | 0.625 | 0.625 | 0.625 | 0.625 |
| Propylene Carbonate | 0.063 | 0.063 | 0.063 | 0.063 | 0.063 | 0.063 | 0.063 |
| Fragrance | 1 | 1 | 1 | 1 | 1 | 1 | 1 |
| Calcium Chloride | 2.238 | 2.238 | 2.238 | 2.238 | 2.238 | 2.238 | 2.238 |
| Potassium Alum | 2.928 | 2.928 | 2.928 | 2.928 | 2.928 | 2.928 | 2.928 |
| *Aloe Barbadensis* leaf juice | — | 0.08 | — | 0.08 | 0.08 | — | — |
| Magnesium Hydroxide | — | — | 0.2 | 0.2 | — | — | — |
| Calcium Hydroxide | — | — | — | — | 0.25 | 0.38 | 0.51 |
| CAP40* | 84 | 84 | 84 | 84 | 84 | 84 | 84 |

*Chemical names are given, with trade names as indicated in Table 1; the only exception is "CAP40", which is a trade name for butane, isobutane, propane propellant.

The cyclomethicone, Finsolv TN, Bentone 38V and sunflower seed oil (with Aloe Vera if used) were mixed for 2 minutes using a 1 inch diameter head Silverson homogeniser operating at 6000 rpm. The propylene carbonate and fragrance were then added with continued mixing at 6000 rpm for a further 5 minutes. The CaCl$_2$ powder was then gradually added over about 2 minutes, followed by the alum, with continued mixing at 6000 rpm. The Inorganic base (if used) was then added, ensuring good homogenisation. The agitation speed was then increased to 6500 rpm for a further 4 minutes, following which, each composition was poured into a sealable container. Following cooling to ambient temperature, 16 parts of each "base" was transferred into an aerosol can and 84 parts of the indicated propellant was added and the can was sealed with an aerosol valve using standard methods.

The antiperspirant efficacy of the aerosol compositions was investigated by the same method as with the sticks except that the aerosol compositions were applied using a 2 second spray (corresponds to approximately 2-2.5 g of the composition, inclusive of the propellant).

The irritation potential of the aerosol compositions were measured in a similar way to those of the sticks except that 4 applications were made per day instead of 3 and panellists applied approximately a 2 second spray (about 2-2.5 g product).

Results of hot-room and Irritation testing are given in Table 4.

TABLE 4

| Example | Mole ratio base:alum | SWR (%) | Adverse events |  | Irritation score |  |
|---|---|---|---|---|---|---|
|  |  |  | 11 days | 29 days | 11 days | 29 days |
| B | not applicable | — | 6 | 13 | 1.95 | 2.17 |
| C | not applicable | 45 | 7 | 13 | 2.05 | 1.98 |
| 4 | 1:2.8 | 43 | 2 | 7 | 1.33 | 1.43 |
| 5 | 1:2.8 | 40 | 5 | 6 | 1.32 | 1.47 |
| 6 | 1:2.8 | 40 | 3 | 7 | 1.39 | 1.44 |
| 7 | 1:1.82 | 35 | 0 | 5 | 1.24 | 1.41 |
| 8 | 1:1.37 | 39 | 2 | 4 | 1.21 | 1.37 |

The results show that Comparative Examples B and C gave relatively high levels of irritation and that the presence of sunflower seed oil and Aloe Vera in Comparative Example C did not mitigate this problem. Addition of magnesium hydroxide to give Examples 4 and 5 did, however, lead to significantly reduced irritation. The results from Examples 6 to 8 indicate that a similar benefit was obtained on addition of calcium hydroxide across a range of base:alum molar ratios.

The invention claimed is:

1. An antiperspirant composition having less than 2% free water and comprising a first salt that is potassium aluminium sulphate and a second salt that is calcium chloride, wherein the first salt and the second salt are formulated or contained in a manner that prevents physical interaction between these two components prior to their application and wherein the product also comprises a third salt which is an inorganic base selected from magnesium hydroxide and calcium hydroxide, the molar ratio of calcium chloride to alum salt being at least 1:1 and the molar ratio of the first salt to the third salt being from 1.2:1 to 4:1.

2. The antiperspirant composition according to claim 1, wherein the first salt has a water content of less than 35% by weight.

3. The antiperspirant composition according to claim 1, wherein the second salt has a water content of less than 15%.

4. The antiperspirant composition according to claim 1, comprising a cosmetically acceptable liquid carrier material having less than 2% by weight free water.

5. The antiperspirant composition according to claim 4, wherein the liquid carrier material comprises a hydrophobic liquid.

6. The antiperspirant composition according to claim 4, wherein the liquid carrier material comprises an emollient oil selected from sunflower seed oil and other unsaturated triglyceride oils.

7. The antiperspirant composition according to claim 1, wherein the first salt has a water content of less than 28% by weight.

8. The antiperspirant composition according to claim 1, wherein the first salt has a water content of less than 20% by weight.

9. The antiperspirant composition according to claim 1 wherein the second s has a water content of less than 8%.

10. The antiperspirant composition according to claim 1 that contains less than 0.5% by weight free water.

11. The antiperspirant composition according to claim 1 wherein the molar ratio of the second salt to the first salt is from 1:1 to 5:1.

12. The antiperspirant composition according to claim 1 wherein the molar ratio of the second salt to the first salt is from 3:2 to 3:1.

\* \* \* \* \*